United States Patent [19]
Bastyr et al.

[11] Patent Number: 5,407,420
[45] Date of Patent: Apr. 18, 1995

[54] FULLY ADJUSTABLE SHOULDER BRACE

[75] Inventors: Charles A. Bastyr; David B. Winer, both of San Diego; Theodore V. Tillinghast, III, Carlsbad; Stephen O. Ross, Vista, all of Calif.

[73] Assignee: Smith & Nephew Donjoy, Inc., Carlsbad, Calif.

[21] Appl. No.: 975,608

[22] Filed: Nov. 12, 1992

[51] Int. Cl.$^6$ .............................................. A61F 5/00
[52] U.S. Cl. .................................... 602/5; 602/16; 602/20
[58] Field of Search ............... 602/4, 5, 20, 21, 16; 128/878, 879, 845

[56] References Cited

U.S. PATENT DOCUMENTS

| | | | |
|---|---|---|---|
| 1,257,297 | 2/1918 | Brown | 602/16 |
| 2,229,271 | 1/1941 | Anderson | 602/20 |
| 2,242,003 | 5/1941 | Lorenzo | 128/92 |
| 2,267,925 | 12/1941 | Johnston | 128/92 |
| 2,414,882 | 1/1947 | Longfellow | 128/92 |
| 2,570,465 | 10/1951 | Lundholm | 128/92 |
| 2,614,558 | 10/1952 | Lovell | 602/20 |
| 2,697,433 | 12/1952 | Zehnder | 128/83 |
| 3,351,054 | 11/1967 | Florek | 128/83 |
| 3,892,232 | 7/1975 | Neufeld | 128/92 |
| 3,896,500 | 7/1975 | Rambert et al. | 623/13 |
| 4,140,111 | 2/1979 | Morrill | 128/92 E |
| 4,237,873 | 12/1980 | Terry | 602/20 |
| 4,241,731 | 12/1980 | Pauley | 602/4 |
| 4,381,770 | 5/1983 | Neufeld | 128/92 BA |
| 4,383,527 | 5/1983 | Asnis et al. | 128/92 EB |
| 4,400,833 | 8/1983 | Kurland | 623/13 |
| 4,441,563 | 4/1984 | Walton, II | 173/163 |
| 4,450,835 | 5/1984 | Asnis et al. | 128/92 EB |
| 4,456,010 | 6/1984 | Reimels et al. | 128/310 |
| 4,463,753 | 8/1984 | Gustilo | 128/92 B |
| 4,467,478 | 8/1984 | Jurgutis | 3/1 |
| 4,476,861 | 10/1984 | Dimakos et al. | |
| 4,509,516 | 4/1985 | Richmond | 178/303 R |
| 4,512,344 | 4/1985 | Barber | 128/755 |
| 4,535,768 | 8/1985 | Hourahane et al. | |
| 4,537,185 | 8/1985 | Stednitz | 128/92 B |

(List continued on next page.)

FOREIGN PATENT DOCUMENTS 645252 of 0000 Canada .
0282789 of 0000 European Pat. Off. .
0384098 of 0000 European Pat. Off. .
1548276 of 0000 France .

(List continued on next page.)

OTHER PUBLICATIONS

Kariya and Kurosawa: *Arthroscopically Aided Anterior Cruciate Ligament Reconstruction Using a New Drill Wire Guide*, 1989, The Journal of Arthroscopic and Related Surgery, vol. 5, No. 3, pp. 227–231.

Hanson and Frost; *A Simple Suture Passer for Use in Cruciate Ligament Repair in the Knee*, 1977, Clinical Orthopaedics and Related Research, pp. 45–46.

Jones; *Results of Use of the Central One-Third of the Patellar Ligament to Compensate for Anterior Cruciate Ligament Deficiency*, 1980, Clinical Orthopaedics and Related Research, pp. 39–44.

Odensten and Gillquist; *A Modified Technique for Anterior Cruciate Ligament (ACL) Surgery Using a New Drill Guide for Isometric Positioning of the ACL*, 1976, Clinical Orthopaedics and Related Research, pp. 154–158.

(List continued on next page.)

Primary Examiner—Michael A. Brown
Attorney, Agent, or Firm—Rodney F. Brown

[57] ABSTRACT

An adjustable shoulder brace is provided for stabilizing and immobilizing the shoulder following an injury or surgical trauma to the soft tissue thereof. The shoulder brace is mountable on the arm and torso to isolate the shoulder and is fully adjustable across the abduction, flexion and rotation ranges of motion of the shoulder to enable fixation of the shoulder in virtually any rehabilitative position. The brace is made up of a series of rigid support members secured to the body of the patient, and a plurality of selectively rotatable and lockable joints adjustably interconnecting the support members. The combined effect of the joints simulates the entire range of motion of the shoulder.

24 Claims, 5 Drawing Sheets

U.S. PATENT DOCUMENTS

| | | |
|---|---|---|
| 4,549,538 | 10/1985 | Schadrack, III et al. ...... 128/92 EB |
| 4,580,563 | 4/1986 | Gross . |
| 4,590,929 | 5/1986 | Klein . |
| 4,605,414 | 8/1986 | Czajka ................................. 623/13 |
| 4,632,100 | 12/1986 | Somers et al. ..................... 128/92 |
| 4,667,664 | 5/1987 | Taylor et al. . |
| 4,668,233 | 5/1987 | Seedhom et al. ..................... 623/13 |
| 4,712,542 | 12/1987 | Daniel et al. ......................... 623/13 |
| 4,723,546 | 2/1988 | Zagorski . |
| 4,738,255 | 4/1988 | Goble . |
| 4,739,751 | 4/1988 | Sapega et al. . |
| 4,744,793 | 5/1988 | Parr et al. ............................ 623/13 |
| 4,772,286 | 9/1988 | Goble et al. ......................... 623/13 |
| 4,773,417 | 9/1988 | Moore et al. . |
| 4,781,182 | 11/1988 | Purnell et al. .................. 128/92 VD |
| 4,784,126 | 11/1988 | Hourahane ............................ 128/92 |
| 4,787,377 | 11/1988 | Laboureau .................... 128/92 VD |
| 4,790,850 | 12/1988 | Dunn et al. ......................... 623/13 |
| 4,823,780 | 4/1989 | Odensten et al. ............ 128/92 VD |
| 4,828,562 | 5/1989 | Kenna ................................. 623/13 |
| 4,872,451 | 10/1989 | Moore et al. ................... 128/92 YF |
| 4,881,537 | 11/1989 | Henning ............................... 623/13 |
| 4,883,048 | 11/1989 | Purnell et al. .................. 128/92 VD |
| 4,901,711 | 2/1990 | Goble et al. ......................... 606/98 |
| 4,911,154 | 3/1990 | Vickers .............................. 606/104 |
| 4,920,958 | 5/1990 | Walt et al. ............................ 606/96 |
| 4,927,421 | 5/1990 | Goble et al. .......................... 606/73 |
| 4,946,462 | 8/1990 | Watanabe ............................ 606/148 |
| 4,950,270 | 8/1990 | Bowman et al. ...................... 606/72 |
| 4,969,895 | 11/1990 | McLeod et al. ....................... 606/96 |
| 5,002,545 | 3/1991 | Whiteside et al. ..................... 606/80 |
| 5,139,499 | 8/1992 | Small et al. ........................... 606/73 |
| 5,139,520 | 8/1992 | Rosenberg ............................ 623/13 |
| 5,167,612 | 12/1992 | Bonutti ................................. 602/5 |

FOREIGN PATENT DOCUMENTS

| | | |
|---|---|---|
| 2194445 | of 0000 | United Kingdom . |
| 940375 | of 0000 | U.S.S.R. . |
| 1197654 | of 0000 | U.S.S.R. . |

OTHER PUBLICATIONS

Beyer; *A Unitunnel Technique for Arthroscopic Anterior Cruciate Ligament Reconstruction*, 1988, Bulletin of the Hospital for Joint Diseases Orthopaedic Institute, vol. 48, No. 2, pp. 164–169.

Rosenoff, Antelyes, and Buonavita; *A Modified Intramedullary Pin for Placement of a Prosthetic Cruciate Ligament*, Sep. 1, 1966, Journal Amer. Veterinary Medical Assoc., pp. 523–524.

Burnett and Fowler; *Reconstruction of the Anterior Cruciate Ligament: Historical Overview*, Jan. 1985, Orthopedic Clinics of North America, vol. 16, No. 1, pp. 143–157.

Verheyden; *An Inexpensive Wire Passer*, Dec. 1986, Plastic Reconstruction Surgery, pp. 820–821.

Raunest; *Application of a New Positioning Device for Isometric Replacement in Anterior Cruciate Ligament Repair and Reconstruction*, Feb. 1991, The Journal of Trauma, vol. 31, No. 2, pp. 223–229.

Matthews, Martin, and Wolock; *Accurate Tunnel Placement Using Drill Guides in Knee Ligament Reconstruction*, Dec. 1, 1989, Orthopaedic Review, vol. XIX, No. 9, pp. 822–824.

Bassi and Fioriti; *A New Guide in the Surgical Reconstruction of the Cruciate Ligaments*, Jun. 1990, Italian Journal of Orthopaedics and Traumatology, pp. 215–219.

McGinty; *Arthroscopic Surgery*, 1985, Techniques on Orthopaedics, vol. 5, Chap. 6, pp. 63–84.

*Technique for Endoscopic Patellar Tendon Bone Block Fixation Using a Cannulated Interference Screw System.*

Richards; *Orthopaedic Catalog*, Richards Manuf. Co., Inc. Memphis, Tenn., 1981 p. 145.

Goble; *Fluoroarthroscopic Allograft Anterior Cruciate Reconstruction*, Techniques Orthop 1988, 2(4):65–73 (1988), 2(4): 65–73.

Edelman; *Arthroscopic Bankart Suturing Yields Better External Rotation*, Orthopedics Today, 26–26 (Feb. 1989).

Statak; *Soft Tissue Attachment Device*, by Zimmer, Inc. 1988.

Arthroscopic Technique for Anterior Cruciate Reconstruction, by Acufex Microsurgical, Inc. 1988.

*Technique for Rear Entry ACL Guide*, by Acufex Microsurgical, Inc. 1988.

Kurosaka, M.; Fixation Screw.

Lambert, K.; *Vascularized Patellar Tendor Graft with Rigid Internal Fixation for Anterior Cruciate Ligament Insufficiency*, Jul. 1982, pp. 85–89.

Kurosaka, et al.,; *A Biomechanical Comparison of Different Surgical Techniques of Graft Fixation in Anterior Cruciate Ligament Reconstruction*, Americal Journal of Sports Medicine, vol. 15, No. 3, 1987, Cleveland, Ohio, pp. 225–229.

Donjoy marketing flyer for the S.C.O.I. Shoulder Brace.

1

FULLY ADJUSTABLE SHOULDER BRACE

TECHNICAL FIELD

The present invention relates to an orthopedic shoulder brace, and particularly to an adjustable orthopedic shoulder brace having a plurality of rotatable and lockable joints for positioning the shoulder at selected angles of abduction, flexion and rotation.

BACKGROUND OF THE INVENTION

Treatment of a shoulder following an injury or surgical trauma typically requires immobilization of the shoulder for an extended period of time. A common means of immobilizing the damaged shoulder during rehabilitation thereof is to place the arm connected to the damaged shoulder in a sling and secure the sling to the torso of the patient by a strap. Although the secured sling effectively immobilizes the shoulder, the sling only enables immobilizing the shoulder in essentially one position against the body.

The shoulder is a relatively complex body joint having several ranges of angular motion, i.e., abduction, flexion and rotation. It has been found that effective rehabilitation of the shoulder requires attention to positioning of the shoulder with respect to all of these ranges of angular shoulder motion. Accordingly, it is desirable to immobilize the shoulder in a manner that provides for adjustment of the shoulder position throughout the rehabilitation.

A body cast enclosing the arm, shoulder and torso has been used for selectively positioning the shoulder at abduction, flexion and rotation angles other than those afforded by a sling. Obviously, however, a body cast is extremely uncomfortable to the patient and cannot be adjusted to other positions without entirely recasting the patient. Furthermore, body casts unduly limit certain desired mobility of the patient, otherwise detracting from rehabilitation of the shoulder. In addition, body casts hinder the ability of the patient to maintain good personal hygiene because they obstruct access to the axilla.

Accordingly, efforts have been made to develop an easily removable and adjustable shoulder brace. One such brace is commercially available which provides an adjustable range of the shoulder abduction angle. The brace employs anterior and posterior rigid support bars which extend from the hip of the patient to the axilla where each is joined anteriorly and posteriorly by selectively rotatable and lockable joints to anterior and posterior rigid support bars extending the length of the upper arm.

Although this brace provides obvious advantages over a sling or a cast, it has nevertheless been found to be uncomfortable for the patient to wear for long periods of time, particularly when sitting against a back support or sleeping on the back because of the rigid posterior components. Furthermore, the brace does not provide for adjustment of the shoulder flexion or rotation angles during rehabilitation.

As such, it is an object of the present invention to provide a shoulder brace that is relatively comfortable when mounted on a patient, even for extended periods of time. It is another object of the present invention to provide a shoulder brace that reduces interference with a patient's ability to sit or recline against the back. It is still another object of the present invention to provide a shoulder brace that reduces obstruction of the axilla, thereby permitting the patient to practice good personal hygiene.

It is a further object of the present invention to provide a shoulder brace that enables adjustable positioning of the shoulder. It is yet another object of the present invention to provide a shoulder brace that provides independently adjustable positioning of the shoulder across all three ranges of angular motion, i.e., the shoulder abduction, flexion and rotation angles.

SUMMARY OF THE INVENTION

The present invention is a fully adjustable orthopedic shoulder brace for stabilizing and immobilizing the shoulder of a patient in furtherance of the objects set forth above. The brace has specific utility for rehabilitation of the shoulder following an injury or surgical trauma, and in particular following an injury or surgical trauma to the soft tissue of the shoulder. The shoulder brace maintains the shoulder relatively comfortably and unobtrusively in a fixed, yet adjustable, position that facilitates rehabilitation of the shoulder throughout the healing period, and particularly during the acute rehabilitation phase immediately following an injury or surgery.

The adjustable shoulder brace of the present invention is mountable on the arm and torso of a human patient to isolate the connective shoulder therebetween. The body-mounted brace is fully adjustable across the three ranges of motion of the shoulder, i.e., abduction, flexion and rotation, to enable fixation of the shoulder in virtually any rehabilitative position. The brace is a support assembly comprising a series of rigid support members secured to the body of the patient, and a plurality of selectively rotatable and lockable joints adjustably interconnecting the support members. Although each joint is only rotatable within a single plane, the combination of three such joints in series simulates the entire range of motion of the shoulder. The components of the brace are described hereafter in the context of the body parts with which they align and interact.

The support members include a rigid torso bar and a rigid upper arm linkage. The torso bar has a hip cuff attached to it which, in concert with a plurality of straps, secures the distal end of the torso bar to the hip of the patient, thereby maintaining the torso bar in a fixed position relative to the torso. The secured torso bar accordingly extends from the hip to the axilla. The upper arm linkage similarly has a cuff attached to it which, in concert with a plurality of straps, secures the upper arm linkage to the underside of the upper arm, thereby maintaining the upper arm linkage in a fixed position relative to the upper arm. The secured upper arm linkage extends from the axilla to the elbow along the underside of the upper arm.

The proximal end of the torso bar and the proximal end of the upper arm linkage are adjustably connected to one another across an axilla joint assembly positioned anterior to the body at or near the axilla. The axilla joint assembly is made up of a shoulder abduction joint and a shoulder flexion joint in series with the abduction joint being adjacent to the torso bar and the flexion joint being adjacent to the upper arm linkage.

The shoulder abduction joint has a lock mode and a rotation mode of operation. In the rotation mode, the abduction joint is freely rotatable about an axis of abduction rotation to any one of a plurality of shoulder abduction angles in the plane of rotation. The abduction joint can be fixed in a selected shoulder abduction angle when switched from the rotation mode to the lock mode.

The shoulder flexion joint likewise has a lock mode and a rotation mode of operation. In the rotation mode, the flexion joint is freely rotatable about an axis of flexion rotation to any one of a plurality of shoulder flexion angles in the plane of rotation. The flexion joint is fixed in the selected shoulder flexion angle when switched to the lock mode.

The abduction and flexion joints are fixably positioned relative to each other such that the planes of abduction and flexion rotation are at all times aligned substantially perpendicular to each other. The axes of abduction and flexion rotation are likewise aligned perpendicular to each other. The axis of abduction rotation is also aligned perpendicular to the longitudinal axis of its adjacent support member, the torso bar, and similarly the axis of flexion rotation is aligned perpendicular to the longitudinal axis of its adjacent support member, the upper arm linkage.

A shoulder rotation joint is further provided integral with the upper arm linkage. As with the shoulder abduction and flexion joints, the shoulder rotation joint has a lock mode and a rotation mode of operation. In the rotation mode, the joint is freely rotatable about an axis of rotator rotation to any one of a plurality of angles in the plane of rotation. The rotation joint is fixed in the selected shoulder rotator angle when switched from the rotation mode to the lock mode.

Unlike the other joints, however, the shoulder rotation joint has an axis of rotation that is collinear with the longitudinal axis of its adjacent support member, the upper arm linkage. It is further noted that the axis of shoulder rotator rotation is aligned substantially perpendicular to the axis of shoulder flexion rotation at all times.

The support members further includes a forearm bar. The forearm bar has a cuff attached to it which, in concert with a plurality of straps, secures the forearm bar to the underside of the forearm, thereby maintaining the forearm bar in a fixed position relative to the forearm. The secured forearm bar extends from the elbow to the wrist along the underside of the forearm. The distal end of the upper arm linkage and the proximal end of the forearm bar are adjustably connected to one another across an elbow flexion joint having a configuration and operating modes similar to the shoulder abduction and flexion joints. The elbow flexion joint is, thus, freely rotatable in the rotation mode and fixable at a selected elbow flexion angle in the lock mode.

The present invention will be further understood, both as to its structure and operation, from the accompanying drawings, taken in conjunction with the accompanying description, in which similar reference characters refer to similar parts.

DESCRIPTION OF PREFERRED EMBODIMENTS

Figure 1:
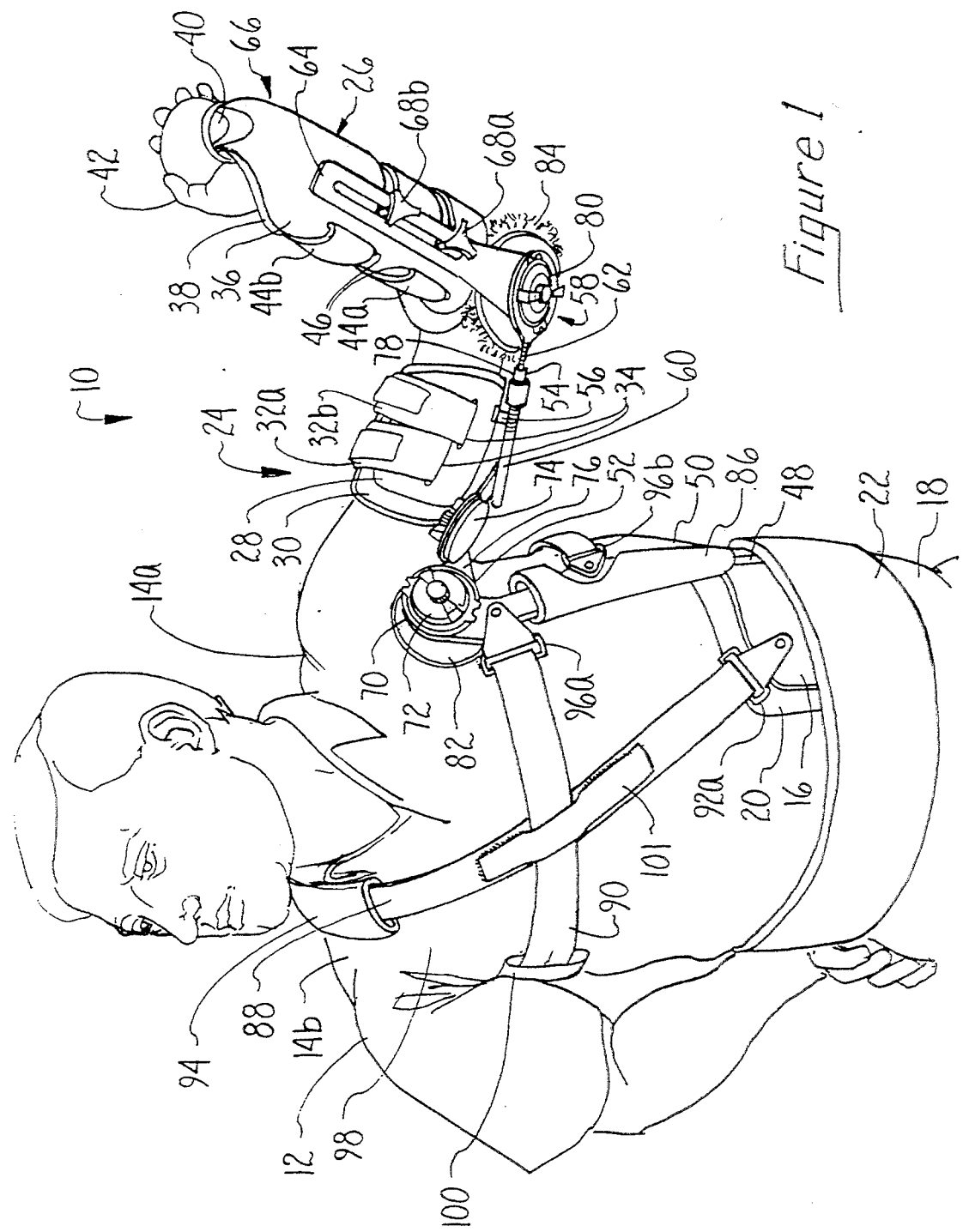
FIG. 1 is an anterior perspective view of the adjustable shoulder brace of the present invention mounted on the body of a patient.

Referring initially to FIG. 1, the adjustable shoulder brace of the present invention, generally designated 10, is shown mounted on the body 12 of a patient. The brace 10 is described hereafter with the shoulder 14a serving as a reference point, such that elements of the brace 10 located near the shoulder 14a are termed "proximal" and elements of the brace 10 located away from the shoulder 14a are termed "distal". It is further noted that although the brace 10 described hereafter is configured for rehabilitative treatment of the shoulder 14a, it is apparent to one skilled in the art that the brace 10 can be readily adapted for similar rehabilitative treatment of the opposite shoulder 14b.

The brace 10 is mounted on the body 12 by means of a support assembly comprising a plurality of cuffs, including a hip cuff 16 formed from a stiffened sheet of plastic that is nevertheless sufficiently flexible to conform to the contour of the hip 18 engaged by the cuff 16. A foam hip pad 20 is positioned between the hip 18 and hip cuff 16 for the comfort of the patient. The hip pad 20 is attached to the hip cuff 16 by a conventional hook and loop fastener, commonly termed a VELCRO fastener.

A padded belt 22 is tightly fastened around the midsection of the patient over the hip cuff 16 and pad 20, thereby pressing the cuff 16 and pad 20 firmly against the hip 18 in conformance therewith to secure the brace 10 at the hip 18. The belt 22 is fastened to itself and to the hip cuff 16 by means of VELCRO fasteners.

The brace 10 is further secured to the body 12 at the upper arm 24 and forearm 26 of the patient. An upper arm cuff 28 is provided to engage the upper arm 24. The upper arm cuff 28, like the hip cuff 16, is formed from a stiffened sheet of plastic that is conformable to the body contours engaged by the cuff 28. The cuff 28 is also provided with an upper arm foam pad 30 that is positioned between the upper arm 24 and cuff 28 and is attached to the upper arm cuff 28 by a VELCRO fastener.

A pair of flexible cloth upper arm straps 32a, 32b are threaded through slots 34 in the cuff 28 and tightly fastened around the upper arm 24 over the cuff 28 and pad 30, thereby pressing the cuff 28 and pad 30 firmly against the upper arm 24 in conformance therewith to secure the brace 10 at the upper arm 24. The straps 32a, 32b are fastened to themselves and to the upper arm cuff 28 by means of VELCRO fasteners.

A forearm cuff 36 is provided to engage the forearm 26. The forearm cuff 36 is formed from a rigid sheet of metal that is preformed to conform to the body contours engaged by the cuff 36. Like the upper arm cuff 28, the forearm cuff 36 is provided with a foam forearm pad 38 that is positioned between the forearm 26 and attached to the forearm cuff 36 by a VELCRO fastener. A spherical foam hand bolster 40 is attached to the distal end of the forearm cuff 36 to provide support for the hand 42. The bolster 40 also provides a means for exercising the arm while the shoulder 14a is immobilized by firmly gripping the bolster 40 with the hand 42.

A pair of flexible cloth forearm straps 44a, 44b are threaded through slots 46 in the cuff 36 and tightly fastened around the forearm 26 over the cuff 36 and pad 38, thereby pressing the cuff 36 and pad 38 firmly against the forearm 26 to secure the brace 10 at the forearm 26. The straps 44a, 44b are fastened to themselves and to the forearm cuff 36 by means of VELCRO fasteners.

The above-described cuffs 16, 28, and 36 are interconnected by means of a plurality of rigid support members joined across a plurality of selectively rotatable and lockable joints. Specifically, a rigid torso bar 48 formed from a strong lightweight material, such as aluminum or a composite, is distally attached to the hip cuff 16 and extends upward from the hip 18 along the anterior of the torso 50 to the anterior of the axilla 52. Adjustable attachment of the torso bar 48 to the hip cuff 16 is provided in a manner described hereafter to enable fitting of the brace 10 to different body sizes.

A rigid metal upper arm linkage 54 is attached to the upper arm cuff 28 in a freely rotatable manner by means of a rotatable mounting assembly 56. The linkage 54 extends away from the axilla 52 along the underside of the upper arm 24 to the elbow 58. The linkage 54 comprises a female bar 60 having a male bar 62 extending therefrom to provide telescopic adjustment of the length of the linkage 54 in a manner described hereafter, thereby enabling fitting of the brace 10 to different arm lengths.

A rigid metal forearm bar 64 is attached to the forearm cuff 36 and extends away from the elbow 58 along the underside of the forearm 26 to the wrist 66. Adjustable attachment of the forearm bar 64 to the forearm cuff 36 is provided by selectively releasable knobs 68a, 68b in a manner described hereafter to further enable fitting of the brace 10 to different arm lengths.

A joint assembly 70 proximally joins the torso bar 48 to the upper arm linkage 54 at the anterior of the body 12 near the axilla 52. The joint assembly 70 comprises a shoulder abduction joint 72 at the proximal end of the torso bar 48 and a shoulder flexion joint 74 at the proximal end of the upper arm linkage 54. The joints 72 and 74 are orthogonally connected across a union member 76. A shoulder rotation joint 78 integral with the upper arm linkage 54 is further to rotatably connect the female bar 60 and the male bar 62. Finally, an elbow flexion joint 80 joins the distal end of the upper arm linkage 54 to the proximal end of the forearm bar 64 at the underside of the elbow 58.

For the comfort of the patient, a foam pad 82 is positioned between the shoulder abduction joint 72 and the axilla 52, and is attached to underside of the abduction joint 72 by a VELCRO fastener. Similarly, a fleece-covered foam pad 84 is positioned between the elbow flexion joint 80 and the elbow 58 and is attached to the underside of the joint 80 by a VELCRO fastener. A foam pad 86 is also fitted around the torso bar 48 for the comfort of the patient.

Figure 2:
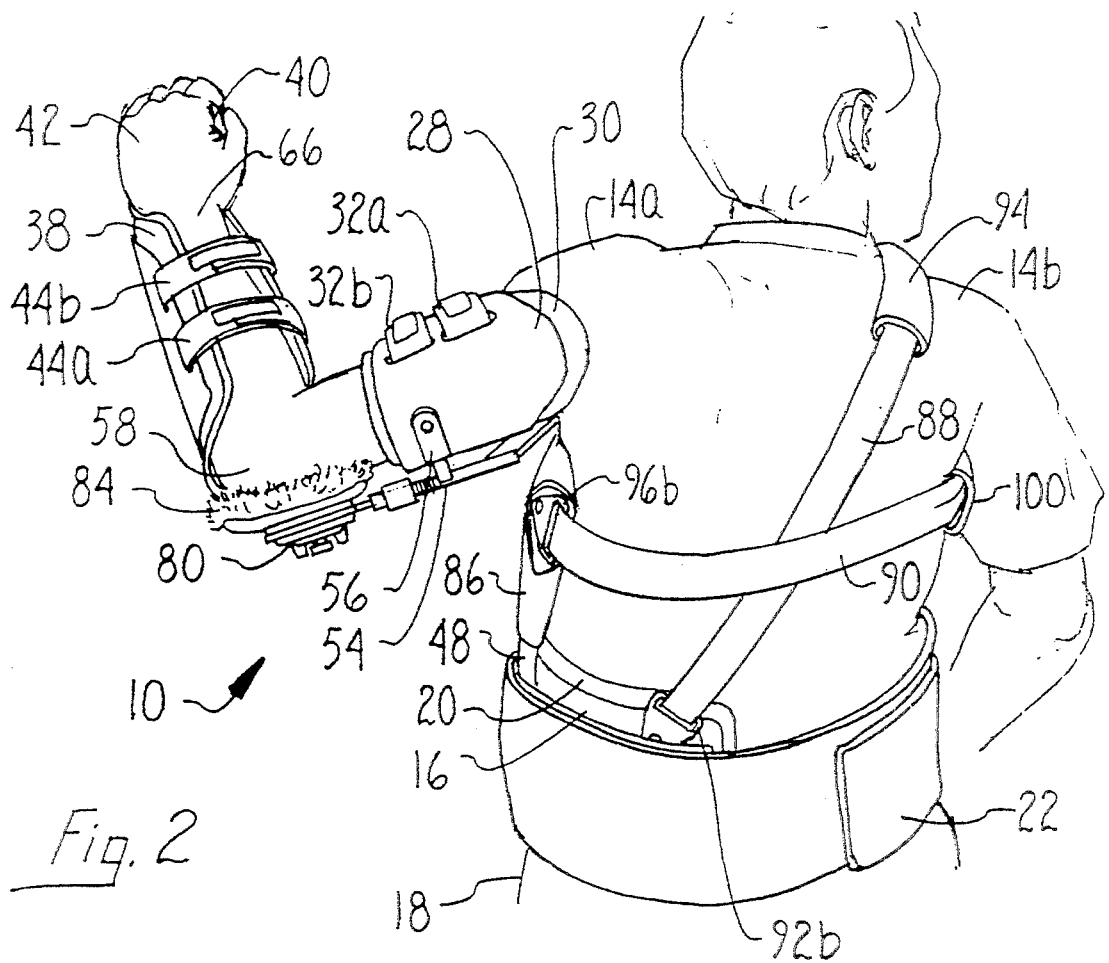
FIG. 2 is a posterior perspective view of the adjustable shoulder brace of FIG. 1 mounted on the patient.

Mounting of the brace 10 on the body 12 is additionally secured by a flexible cloth shoulder strap 88 and chest strap 90. The shoulder strap 88 passes through a first strap loop 92a riveted to one edge of the hip cuff 16, over the opposite shoulder 14b of the patient, and through a second strap loop 92b riveted to the opposite edge of the hip cuff 16 as shown in FIG. 2. A foam pad 94 is provided around the strap 88 where it engages the shoulder 14b for the comfort of the patient. The strap 88 is fastened onto itself by VELCRO tabs attached to its ends.

The chest strap 90 passes through a first strap loop 96a riveted to one edge of the torso bar 48, around the chest 98 of the patient, and through a second strap loop 96b riveted to the opposite edge of the torso bar 48. A foam pad 100 is provided around the strap 90 where it engages the right side of the chest 98. The strap 90 is fastened onto itself by VELCRO attached to its ends. Straps 88, 90 overlap on the anterior side of the patient and are secured to one another at the point of overlap by a VELCRO strip 101.

FIG. 2 shows the posterior configuration of the brace 10. It is apparent from FIG. 2 that the posterior of the brace 10 is substantially free of any rigid structural components, thereby enabling the patient to recline or sit posteriorly with a minimum of discomfort. The posterior configuration also provides unobstructed access to the axilla 52 for improved personal hygiene during extended periods of use of the brace 10.

Figure 3:
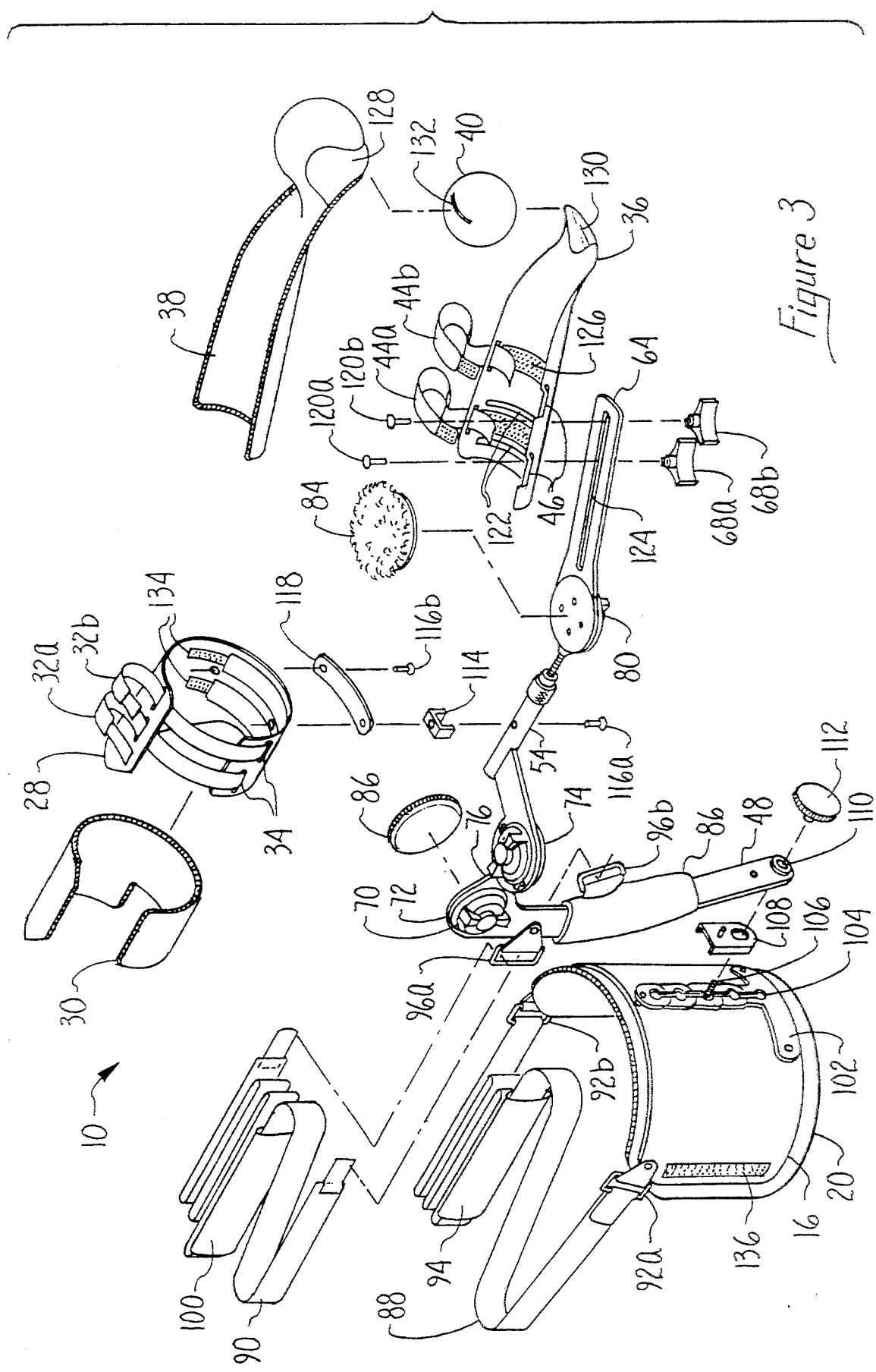
FIG. 3 is an exploded perspective view of the support assembly of the adjustable shoulder brace of FIG. 1.

Referring now to FIG. 3, the support assembly of the shoulder brace 10 is described in greater detail. The support assembly is shown to comprise the torso bar 48, upper arm linkage 54 and forearm bar 64, connected to the hip cuff 16, upper arm cuff 28, and forearm cuff 36, respectively.

Adjustable connection of the torso bar 48 to the hip cuff 16 is provided by a mounting bracket 102 riveted to the hip cuff 16. A longitudinal slot 104 is formed in the mounting bracket 102 to receive a threaded male member 106. The male member 106 extends away from the body through the slot 104, through a swivel-prevention bracket 108 slidably positioned over the mounting bracket 102, and through a distal aperture 110 in the torso bar 48. An adjustment knob 112 having corresponding female threads is threadably attached to the end of the male member 106 extending through the aperture 110.

Selective attachment of the distal end of the torso bar 48 to the hip cuff 16 at any point along the length of the slot 104 enables adjustment of the distance between the hip cuff 16 and axilla joint assembly 70 for a proper fit of the brace 10. Adjustment of the distance is accomplished by loosening the knob 112 and sliding the male member 106, swivel-prevention bracket 108 and torso bar 48 in unison to the desired point along the slot 104. The knob 112 is then tightened back down onto the torso bar 48 to securely fasten the bar 48 to the hip cuff 16 at that point.

The mounting assembly 56 rotatably attaches the upper arm linkage 54 to the upper arm cuff 28. The mounting assembly 56 comprises a mounting member 114, rivets 116a, 116b, and a stiffener 118. The rivet 116a extends through the upper arm linkage 54, mounting member 114, stiffener 118, and upper arm cuff 28, thereby serving as an axis of rotation to enable free rotation of the cuff 28 about the rivet 116a relative to the linkage 54. The rivet 116b fixes the stiffener 118 to the cuff 28.

Adjustable connection of the forearm bar 64 to the forearm cuff 36 is provided by threaded bolts 120a, 120b extending through latitudinal slots 122 in the cuff 36 and through a longitudinal slot 124 in the forearm bar 64. Knobs 68a, 68b have corresponding female threads that are threadably attached to the ends of the bolts 120a, 120b, respectively, extending through the slot 124. The position of the forearm cuff 36 on a patient can be adjusted for a proper fit of the brace 10 by loosening the knobs 68a, 68b and sliding the bolts 120a, 120b and cuff 36 in unison to the desired point along the slot 124. The knobs 68a, 68b are then tightened back down onto the forearm bar 64 to securely fasten the bar 64 to the forearm cuff 36 at that point.

A plurality of VELCRO fasteners 126 are provided on the inner side of the forearm cuff 36 to fasten the forearm pad 38 and straps 44a, 44b thereto. The forearm pad 38 also has a pocket 128 formed in its distal end which receives and secures the spherical bolster 40. The bolster 40 is further secured to the forearm cuff 36 by inserting a hooked distal end 130 of the cuff 36 into a slit 132 in the bolster 40.

A plurality of VELCRO fasteners 134 are likewise provided on the inner side of the upper arm cuff 28 to fasten the upper arm pad 30 and straps 32a, 32b thereto. Although not shown, VELCRO fasteners are similarly positioned on the inner side of the hip cuff 16 to fasten the hip pad 20 thereto and on the inner side of the joints 72 and 80 to fasten pads 86 and 84, respectively, thereto. It is further noted that VELCRO tabs are provided on the ends of all straps 32a, 32b, 44a, 44b, 88, 90, as well as the belt 22 (not shown in FIG. 3) to enable fastening of the respective straps and belt onto themselves. VELCRO fasteners 136 are also provided on the outer side of the hip cuff 16 to fasten the belt 22 to the cuff 16.

Figure 4A:
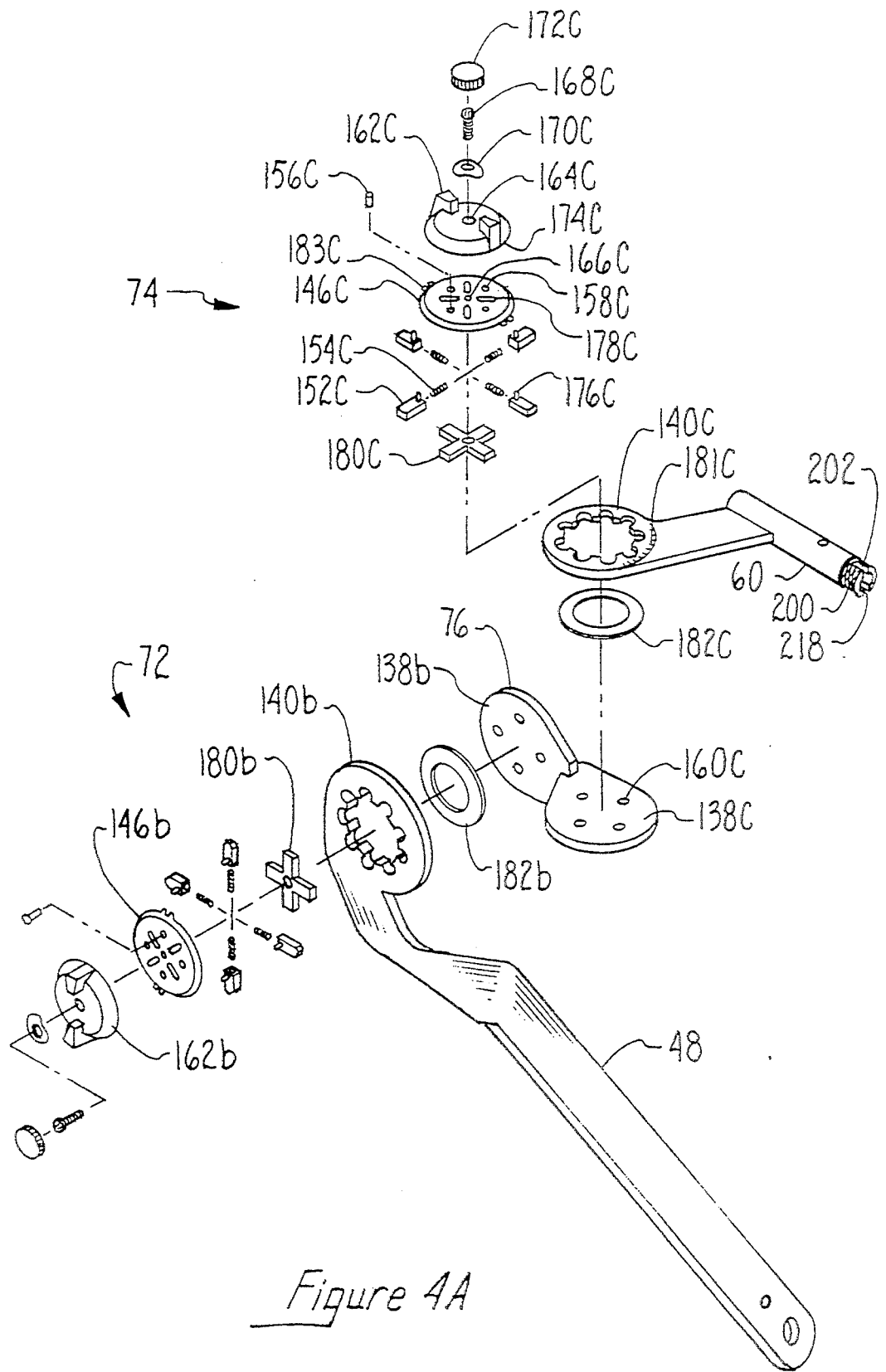
FIGS. 4A and 4B are an exploded perspective view of the rotatable and lockable joints of the adjustable shoulder brace of FIG. 1 divided into two figures at the junction of the axilla joint assembly and the upper arm linkage.
Figure 4B:
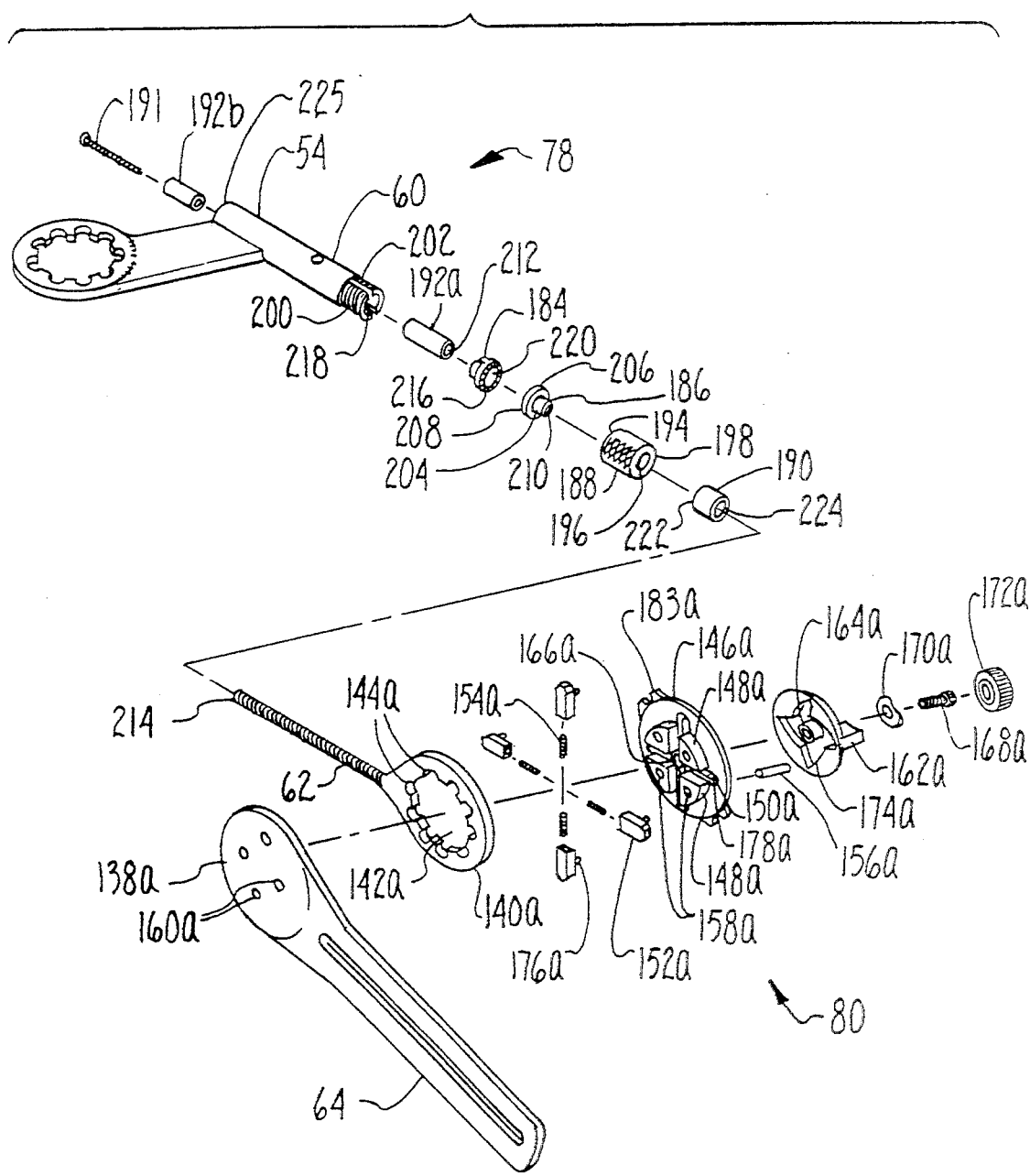

Referring now to FIGS. 4A and B, the internal components of the joints of the shoulder brace 10 are described. Because the joints 72, 74, and 80 have substantially the same components, the description hereafter of the elbow flexion joint 80 applies likewise to the shoulder abduction and flexion joints 72, 74, except where otherwise noted. Common components of the joints 72, 74, 80 are identified by common reference numbers, differing only by the letter suffix. As such, the components of the elbow flexion joint 80 are identified by the suffix "a", while common components of the shoulder abduction and flexion joints 72 and 74 are identified by the suffixes "b" and "c", respectively.

The elbow flexion joint 80 rotatably connects the forearm bar 64 and upper arm linkage 54, and enables selective locking of the joint 80 in a desired angle of elbow flexion. Accordingly, the proximal end of the forearm bar 64 is provided with a flattened first mounting face 138a and the distal end of the upper arm linkage 54 is provided with a flattened second mounting face 140a abutting flush against the first mounting face 138a.

The second mounting face 140a has a central aperture 142a through it with a plurality of notches 144a formed around the peripheral edge of the aperture 142a at regular 40° intervals. A hub 146a abuts the second mounting face 140a on the opposite side of the first mounting face 138a. The hub 146a has raised interior portions 148a of a sufficiently shortened radial length to enable the interior portions 148a to fit within the aperture 142a entirely clear of the notches 144a.

The raised portions 148a of the hub 146a are separated by recessed oval-shaped channels 150a at regular 90° intervals dividing the hub 146a into quadrants. Each channel 150a has a lock member 152a and a spring 154a slidably positioned therein. The radial length of the channels 150a are greater than the radial length of the raised portions 148a, such that the lock members 152a can slide radially outwardly within the channels 150a to selectively engage the notches 144a in a manner described hereafter.

The mounting faces 138a, 140a and hub 146a with its attendant lock members 152a and springs 154a are secured in their relative positions by a plurality of rivets 156a extending through holes 158a, 160a positioned to receive the rivets 156a in the hub 146a and face 138a, respectively. A cam knob 162a is mounted atop the hub 146a and has a center hole 164a aligned with a threaded center hole 166a in the hub 146a. A security screw 168a slidably extends through the center hole 164a and is threaded into the center hole 166a of the hub 146a. A spring washer 170a and an adjusting knob 172a are also provided to facilitate tightening and loosening of the security screw 168a.

The cam knob 162a has a continuous recessed interior cam edge 174a that engages a peg 176a integral with and extending from each of the lock members 152a through an opening 178a in the hub 146a above each recessed channel 150a which is sized to prevent the passage of lock member 152a therethrough. As will be shown, placement of the cam knob 162a in one of two positions enables selection of the lock or rotation operating mode of joint 80.

In operation, each lock member 152a and spring 154a is positioned in a channel 150a with the spring 154a abutting the central edge of the channel 150a and biasing the lock member 152a toward the peripheral edge of the channel 150a. The peg 176a extending through the opening 178a engages the cam edge 174a of the cam knob 162a positioned atop the hub 146a. When the cam knob 162a is turned to a first position where the portion of the cam edge 174a abutting the peg 176a is closest to the center hole 166a, the peg 176a is urged radially inward within opening 178a against the force of the spring 154a. Movement of the peg 176a concurrently causes the lock member 152a to slide radially inward within channel 150a until the lock member 152a is clear of any notches 144a. Thus, the joint 80 is positioned in the rotational mode of operation, wherein the forearm bar 64 is free to rotate through all angles of rotation relative to the upper arm linkage 54.

In contrast, when the cam knob 162a is turned to its second position where the portion of the cam edge 174a abutting the peg 176a is furthest from the center hole 166a, the peg 176a is no longer urged radially inward within opening 178a by the cam knob 162a. The spring 154a consequently causes the lock member 152a to slide radially outward within channel 150a until the lock member 152a enters a notch 144a at a selected angle of rotation. The force of the spring 154a and the configuration of the notch 144a and lock member 152a prevent the notch 144a from releasing the lock member 152a until the cam knob 162a is returned to its first position. Thus, the joint 80 is positioned in the lock mode of operation, wherein the forearm bar 64 and upper arm linkage 54 are fixed relative to one another at the selected angle of rotation.

Angle gradations (visible as 181c on joint 74 in FIG. 4A) are placed around the periphery of the second mounting face 140a and reference pointers 183a are formed on the periphery of the hub 146 to facilitate location of the desired elbow flexion angle between the forearm bar 64 and upper arm linkage 54 in the lock mode. The security screw 168a can also be tightened down to prevent inadvertent movement of the cam knob 162a from the second locking position.

It is noted that due to the 40° spacing of the notches 144a and the 90° spacing of the channels 150a, a lock member 152a aligns with a notch 144a at thirty-six different angles of rotation. Accordingly, the joint 80 has angular locking increments of 10° through 360° of rotation.

All of the components recited above are common to the three joints 72, 74, and 80. However, unlike the joint 80, joints 72 and 74 are further provided with cross-shaped spacers 180b, 180c that fit atop the lock members 152b, 152c within channels 150b, 150c, respectively and with flat washers 182b and 182c that fit between the first and second mounting faces 138b and 140b, 138c and 140c, respectively. The joints 72 and 74 nevertheless operate in substantially the same manner as the joint 80. Thus, the shoulder abduction joint 72 provides for selection of a shoulder abduction angle between the torso bar 48 and the upper arm linkage 54. The shoulder flexion joint 74 provides for selection of a shoulder flexion angle between the torso bar 48 and upper arm linkage 54.

The shoulder rotation joint 78 is distinguishable from the joints 72, 74, and 80 described above insofar as the joint 78 is integral with the upper arm linkage 54. As such, the axis of rotation of the joint 78 is collinear with its adjacent support member 54, whereas the axes of rotation of the remaining joints 72, 74, and 80 are perpendicular to the respective adjacent support members 48, 54, or 64.

The shoulder rotation joint 78 comprises the tubular female bar 60 and the externally-threaded hexagonally-shaped male bar 62 both formed from rigid metal. The bars 60 and 62 are adjustably connected to one another by assembly of a pair of gear members 184 and 186, a rotation angle adjustment nut 188, a length adjustment nut 190, a retention screw 191 and a pair of bushings 192a, 192b.

The rotation angle adjustment nut 188 has a relatively large proximal opening 194 and a relatively small distal opening 196 creating a distal shoulder 198 adjacent to the small distal opening 196. The large proximal opening 194 is sized to fit over the distal end 200 of the female bar 60 and has internal threads that are sized to be threadably received by external threads 202 on the distal end 200 of the bar 60. The small opening 196 is sized to receive the tapered distal end 204 of the second gear member 186 which is freely rotatable therein, while the shoulder 198 blocks the widened proximal end 206 of the second gear member 186 from passing through the small opening 196.

The second gear member 186 has a plurality of radial teeth on its proximal face 208 and is provided with a hexagonal bore 210 therethrough, which prevents rotation of the male bar 62 therein, but enables slidable longitudinal movement of the bar 62 therethrough. The bushing 192a has a central opening 212 sized to be slip fitted over the proximal end 214 of the male bar 62 and acts as a bearing surface for rotation of the bar 62.

The first gear member 184 has a plurality of radial teeth on its distal face 216 which are sized to lockingly engage the radial teeth on the proximal face 208 of the second gear member 186 when in abutment therewith. The first gear member 184 is sized to be press fittingly received by the distal opening 218 of the female bar 60 and is provided with a cylindrical bore 220 therethrough which enables free rotation of the male bar 62 therein. The bushing 192a is of sufficient diameter to prevent it from passing through the cylindrical bore 220. The length adjustment nut 190 has a widened proximal opening 222 sized to fittingly receive the tapered end 204 of the second gear member 186 and has a narrowed distal bore 224 therethrough, having internal threads to threadably receive the male bar 62.

The joint 78 is assembled by initially threading the length adjustment nut 190 onto the threads of the male bar 62. The tapered distal end 204 of the second gear member 186 is then inserted through the small distal opening 196 of the rotation angle adjustment nut 188 and the member 186 and nut 188 are slid onto the male bar 62. The distal end 204 of the second gear member 186 is fitted into the proximal opening 222 of the length adjustment nut 190 to couple the rotation and length adjustment nuts 188, 190 to one another, while permitting independent rotation thereof. The first gear member 184 is slid onto the male bar 62 and the bushing 192a is fitted onto the proximal end 214 of the bar 62.

The retention screw 191 is slip fitted through the center of bushing 192b to distally extend therefrom and the screw 191 and bushing 192b are inserted into the open proximal end 225 of the female bar 60 which is in communication with the distal opening 218 across an interior bore. The proximal end 214 of the male bar 62 is inserted into the distal opening 218 of the female bar 60, and the first gear member 184 is press fitted over the distal opening 218. An internally threaded bore (not shown) is provided in the proximal end 214 of the male bar 62 that is threadably engaged by the retention screw 191 to fixedly secure the bushing 192b on the proximal end 214. The bushing 192b is of sufficient outside diameter to prevent distal withdrawal of the male bar 62 past a circumferential ridge (not shown) formed around the inside diameter of the female bar 60.

To operate the joint 78 in the lock mode, the desired angular orientation of the second mounting face 140a, and correspondingly the angular orientation of the entire forearm support assembly, is selected and the rotation adjustment nut 188 is tightened down onto the female bar 60 to engage the radial teeth of the second gear member 186 with the radial teeth of the first gear member 184. To operate in the rotation mode, the rotation adjustment nut 188 is simply loosened until the two sets of radial teeth disengage permitting the male bar 62 to rotate freely relative to the female bar 60.

The length of the upper arm assembly linkage 54 can be adjusted to fit the upper arm of the patient irrespective of the position of the rotation adjustment nut 188 without altering its position. Length adjustment is provided by turning the length adjustment nut 190 in one direction to threadably draw the male bar 62 from the distal opening 218 of the female bar 60 and lengthen the linkage 54. The bushing 192b on the proximal end 214 of the male bar 62 acts as a stop to prevent the male bar 62 from entirely disengaging the female bar 60. Turning the length adjustment nut 190 in the other direction threadably feeds the male bar 62 back into the distal opening 218 of the female bar 60 to shorten the linkage 54.

Figure 5:
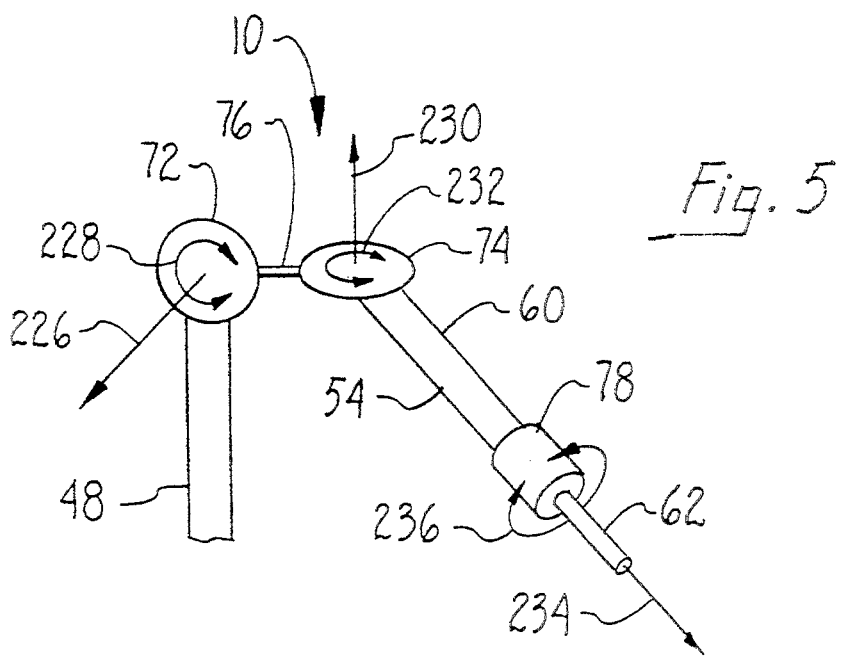
FIG. 5 is a diagrammatic view of the adjustable axes and planes of rotation enabled by the shoulder brace of the present invention.

The adjustable orientation of the brace 10 to simulate the three ranges of motion of the shoulder, i.e., abduction, flexion and rotation, is further described with reference to the schematic representation of the brace 10 in FIG. 5. The adjustable range of shoulder abduction is provided by the shoulder abduction joint 72 which has an axis of abduction rotation represented by an arrow 226 extending perpendicularly relative to the joint 72 and the torso bar 48. Circular arrow 228 contains the range of selectable abduction angles and lies on the plane of abduction rotation. The abduction joint 72 and torso bar 48 also lie within this plane.

The adjustable range of shoulder flexion is provided by the shoulder flexion joint 74 that is connected to the shoulder abduction joint 72 across the union 76. The flexion joint 74 has an axis of flexion rotation represented by an arrow 230 extending perpendicularly relative to the joint 74 and the upper arm linkage 54. Circular arrow 232 contains the range of selectable flexion angles and lies on the plane of flexion rotation. The flexion joint 74 and upper arm linkage 54 also lie within this plane. It is further apparent that the axis of flexion rotation 230 is perpendicular to the axis of abduction rotation 226 and that the plane of flexion rotation 232 is perpendicular to the plane of abduction rotation 228.

The adjustable range of shoulder rotation is provided by the shoulder rotator joint 78 that connects the female bar 60 to the male bar 62 of the upper arm linkage 54. The rotator joint 78 has an axis of rotator rotation represented by an arrow 234 extending collinearly with the longitudinal axis of the upper arm linkage 54. Circular arrow 236 contains the range of selectable rotator angles and lies on the plane of rotator rotation. The plane of rotator rotation 236 is perpendicular to the axis of rotator rotation 234 as well as the plane of flexion rotation 232.

While the forgoing preferred embodiments of the invention have been described and shown, it is understood that alternatives and modifications, such as those suggested and others, may be made thereto and fall within the scope of the invention.

We claim:

1. An adjustable shoulder brace mountable on a human body having a torso and an arm attached thereto at a shoulder, the arm having an upper arm and a forearm attached to the upper arm at an elbow, said shoulder brace comprising:
   a substantially rigid support member;
   means for anchoring said rigid support member to the torso;
   means for supporting the upper arm;
   means for connecting said upper arm support means to said support member;
   means integral with said connecting means for selectively fixing a shoulder abduction angle;
   means integral with said connecting means for selectively fixing a shoulder flexion angle; and
   means integral with said upper arm support means for selectively fixing a shoulder rotation angle.

2. A shoulder brace as recited in claim 1 further comprising:
   means for supporting the forearm;
   means for connecting said forearm support means to said upper arm support means;
   means integral with said forearm support connecting means for selectively fixing an elbow flexion angle.

3. A shoulder brace as recited in claim 1 wherein said shoulder flexion angle selecting means is a shoulder flexion joint having a lock mode and a rotation mode of operation, further wherein said shoulder flexion joint is freely rotatable in said rotation mode to any one of a plurality of shoulder flexion angles on a plane of flexion rotation and fixable in said lock mode to any one of said plurality of shoulder flexion angles.

4. A shoulder brace as recited in claim 3 wherein said shoulder abduction angle selecting means is a shoulder abduction joint having a lock mode and a rotation mode of operation, further wherein said shoulder abduction joint is freely rotatable in said rotation mode to any one of a plurality of shoulder abduction angles on a plane of abduction rotation and fixable in said lock mode to any one of said plurality of shoulder abduction angles.

5. A shoulder brace as recited in claim 4 wherein said shoulder flexion joint and said shoulder abduction joint are aligned such that said plane of flexion rotation is substantially perpendicular to said plane of abduction rotation.

6. A shoulder brace as recited in claim 4 wherein said brace has an anterior face and a posterior face, further wherein said shoulder flexion joint and said shoulder abduction joint are both positioned on said anterior face.

7. A shoulder brace as recited in claim 3 wherein said shoulder rotation angle selecting means is a shoulder rotation joint having a lock mode and a rotation mode of operation, further wherein said shoulder rotation joint is freely rotatable in said rotation mode to any one of a plurality of shoulder rotation angles on a plane of rotator rotation and fixable in said lock mode to any one of said plurality of shoulder rotation angles.

8. A shoulder brace as recited in claim 7 wherein said shoulder flexion joint has an axis of flexion rotation and said shoulder rotation joint has an axis of rotator rotation, further wherein said axis of flexion rotation and said axis of rotator rotation are orthogonally aligned relative to each other such that said plane of flexion rotation is substantially perpendicular to said plane of rotator rotation.

9. A shoulder brace as recited in claim 2 wherein said elbow flexion angle selecting means is an elbow flexion joint having a lock mode and a rotation mode of operation, further wherein said elbow flexion joint is freely rotatable in said rotation mode to any one of a plurality of elbow flexion angles on a plane of elbow flexion rotation and fixable in said lock mode to any one of said plurality of elbow flexion angles.

10. An adjustable shoulder brace mountable on a human body having a torso and an arm attached thereto at a shoulder, the arm having a proximal upper arm and a distal forearm attached to the upper arm at an elbow, said shoulder brace comprising:
    a rigid torso bar having a proximal end and a distal end;
    a rigid upper arm linkage having a proximal end, a distal end and a longitudinal axis; and
    a joint assembly adjustably connecting said torso bar to said upper arm linkage, wherein said joint assembly includes a shoulder abduction joint having a first axis of rotation for selectively fixing a shoulder abduction angle between the upper arm and torso, and a shoulder flexion joint having a second axis of rotation for selectively fixing a shoulder flexion angle between the upper arm and torso.

11. A shoulder brace as recited in claim 10 wherein said first and second axes of rotation are substantially perpendicular.

12. A shoulder brace as recited in claim 10 wherein said joint assembly adjustably connects said proximal end of said torso bar to said proximal end of said upper arm linkage.

13. A shoulder brace as recited in claim 10 further comprising a rigid forearm bar having a proximal end and a distal end, wherein said proximal end of said forearm bar is adjustably connected to said distal end of said upper arm linkage.

14. A shoulder brace as recited in claim 10 further comprising a shoulder rotation joint connected to said upper arm linkage and having a third axis of rotation for selectively fixing a shoulder rotation angle between the upper arm and torso.

15. A shoulder brace as recited in claim 14 wherein said shoulder rotation joint is integral with said upper arm linkage such that said third axis of rotation of said shoulder rotation joint is collinear with said longitudinal axis of said upper arm linkage.

16. A shoulder brace as recited in claim 13 further comprising an elbow flexion joint adjustably connecting said proximal end of said forearm bar to said distal end of said upper arm linkage for selectively fixing an elbow flexion angle between the forearm and upper arm.

17. A shoulder brace as recited in claim 10 wherein said shoulder flexion joint has a lock mode and a rotation mode of operation, further wherein said shoulder flexion joint is freely rotatable in said rotation mode to any one of a plurality of shoulder flexion angles on a plane of flexion rotation and fixable in said lock mode to any one of said plurality of shoulder flexion angles.

18. A shoulder brace as recited in claim 17 wherein said shoulder abduction joint has a lock mode and a rotation mode of operation, further wherein said shoulder abduction joint is freely rotatable in said rotation mode to any one of a plurality of shoulder abduction angles on a plane of abduction rotation and fixable in said lock mode to any one of said plurality of shoulder abduction angles.

19. A shoulder brace as recited in claim 10 wherein said shoulder flexion joint and said shoulder abduction joint are positionable substantially anterior to the body.

20. An adjustable shoulder brace mountable on a human body having a torso and an arm attached thereto at a shoulder, the arm having a proximal upper arm and a distal forearm attached to the upper arm at an elbow, said shoulder brace comprising:

a rigid torso bar having a proximal end and a distal end;

a rigid upper arm linkage having a proximal end, a distal end and a longitudinal axis;

a joint assembly adjustably connecting said proximal end of said torso bar to said proximal end of said upper arm linkage, wherein said joint assembly includes a shoulder abduction joint having a first axis of rotation for selectively fixing a shoulder abduction angle between the upper arm and torso, and a shoulder flexion joint having a second axis of rotation for selectively fixing a shoulder flexion angle between the upper arm and the torso; and a shoulder rotation joint connected to said upper arm linkage and having a third axis of rotation for selectively fixing a shoulder rotation angle between the upper arm and the forearm.

21. A shoulder brace as recited in claim 20 further comprising a rigid forearm bar having a proximal end and a distal end, wherein said proximal end of said forearm bar is adjustably connected to said distal end of said upper arm linkage.

22. A shoulder brace as recited in claim 20 wherein said first and second axes of rotation are substantially perpendicular.

23. A shoulder brace as recited in claim 20 wherein said shoulder rotation joint is integral with said upper arm linkage such that said third axis of rotation of said shoulder rotation joint is collinear with said longitudinal axis of said upper arm linkage.

24. A shoulder brace as recited in claim 20 wherein said shoulder flexion joint and Said shoulder abduction joint are positionable substantially anterior to the body.

* * * * *